United States Patent [19]

Horng et al.

[11] Patent Number: 4,904,824

[45] Date of Patent: Feb. 27, 1990

[54] CHEMICAL PROCESS

[76] Inventors: Liou-Liang Horng, 1731 Wishingwell Dr., Creve Coeur, Mo. 63146; Chung Y. Shen, 12630 Conway Downs Dr., St. Louis, Mo. 63141; Mark E. Jason, 34 Ridge Point Dr., Chesterfield, Mo. 63017

[21] Appl. No.: 236,096

[22] Filed: Aug. 24, 1988

[51] Int. Cl.$^4$ .............................................. C07C 59/22
[52] U.S. Cl. ..................................................... 562/583
[58] Field of Search .......................................... 562/583

[56] References Cited

U.S. PATENT DOCUMENTS

| | | | |
|---|---|---|---|
| 3,635,830 | 1/1972 | Lamberti et al. | 252/89 |
| 3,692,685 | 9/1972 | Lamberti et al. | 252/89 |
| 3,914,297 | 10/1975 | Lamberti et al. | 260/535 P |
| 4,663,071 | 5/1987 | Bush et al. | 252/174.19 |
| 4,689,167 | 8/1987 | Collins et al. | 252/95 |

OTHER PUBLICATIONS

Chemical Abstracts, vol. 60, 2295G, 1964.
Chemical Abstracts, vol. 64, 4224G, 1966.

*Primary Examiner*—Bruce D. Gray
*Attorney, Agent, or Firm*—R. C. Loyer

[57] ABSTRACT

There is disclosed herein improved processes for the preparation of mixtures of alkali metal salts of 1-hydroxy-3-oxa-1,2,4,5-pentane tetracarboxylate and alkali metal salts of 3,6-dioxa-1,2,4,5,7,8-octane hexacarboxylate wherein by-product calcium carbonate produced by the process of making such mixtures is employed in a recycle pattern to prepare additional amounts of mixtures of said compounds.

17 Claims, No Drawings

CHEMICAL PROCESS

This invention relates to a process for making mixtures of ether carboxylic acids and more particularly to processes for making mixtures of 1-hydroxy-3-oxa-1,2,4,5-pentane tetracarboxylic acid and 3,6-dioxa 1,2,4,5,7,8-octane hexacarboxylic acids or salts thereof.

Polycarboxylic acids have long been known to be useful, usually in the salt form, as detergent builders or sequestrants. Also, ether carboxylates useful as metal sequestering and detergent builders have been known and are most desirable for their beneficial effects in laundering applications.

Because these ether carboxylates have such effective sequestering ability they have become attractive in recent times for the replacement of sodium tripolyphosphate which has long been the leading detergent builder or sequesterant. Examples of prior art efforts to provide ether carboxylates detergent builders or sequesterants are found in U.S. Pat. Nos. 3,635,830; 3,692,685 which relate to the use of oxydisuccinic acid salts as detergent builders. Another example of the prior art employing a carboxylate ether is found in U.S. Pat. No. 3,914,927 relating to carboxymethyloxysuccinates.

While these compounds in the prior art have utility as a builder or sequesterant in laundry detergent formulations it has been found that mixtures of certain low molecular weight ether carboxylates are more attractive and cost effective for such utility. In the field of detergent builders and sequesterants for laundry detergent formulations low cost of the components is extremely important because it is a very competitive market. While many ether carboxylate compounds have been found to be useful there is needed more economical manufacturing processes whereby such compounds can be economically produced in large volume.

There has been discovered a mixture of polycarboxylic acids or salts thereof, particularly the sodium salts, of 1-hydroxy-3-oxa-1,2,4,5-pentane tetracarboxylic acid (HOPTC) and 3,6-dioxa-1,2,4,5,7,8-octane hexacarboxylic acid (DOOHC) which are highly useful for detergent formulations as a sequesterant or builder. This mixture is prepared by reaction of a combination of maleate and D,L-tartrate salts catalyzed with calcium ion in strongly basic solution. Large amounts of calcium carbonate are produced as a by-product during purification of the product.

An important requirement of an economical process for producing ether carboxylate salts is the economical means to dispose of waste by-product calcium carbonate in an environmentally acceptable yet economical manner. To provide a more economical process it is desired that a use for such by-product calcium carbonate be found rather than discharging it as waste.

SUMMARY OF THE INVENTION

In accordance with the process of this invention, a mixture of salts, mainly the calcium salt, of maleic acid and D,L-tartaric acid comprising from about 20 to 70% by weight in aqueous solution react together in the presence of salt forming cations of calcium and alkali metal cations.

The above-described aqueous reaction mixture is maintained at a temperature of from about 20° C. to about 120° C. for a time period sufficient to form a reaction product containing a mixture of HOPTC and DOOHC salts. The reaction mixture is treated to remove calcium ion for purposes of utility in detergent compositions such that the molar ratio of calcium to D,L-tartrate succinate products is less than 1:10. The removed calcium cation is recovered and recycled to catalyze additional reactions to produce such product.

In one aspect of this invention the recycle of calcium ion in the process of this invention eliminates the need to dispose of large quantities of solid waste. In another aspect of this invention the recycle of the calcium ion in the form of solid, unwashed filter cake reduces greatly the loss of product otherwise carried out of the production stream when solid waste disposal would be required. In yet another aspect of this invention, raw material requirements, particularly calcium, required to produce the HOPTC/DOOHC mixture are greatly reduced. It has been shown that repeated recycle of calcium ion does not cause any increase in calcium content of the desired HOPTC/DOOHC mixture even though it is critical for detergent use to maintain very low levels of calcium ion in the HOPTC/DOOHC mixture.

DETAILED DESCRIPTION OF THE INVENTION

HOPTC/DOOHC compositions are disclosed in U.S. Pat. No. 4,663,071 to Busch et al and is incorporated herein by reference. It is noted in the patent referred to above that the calcium cations in aqueous reaction mixtures catalyze the reaction. It has been previously known to employ the catalytic calcium in the form of calcium hydroxide since an alkaline agent was also required. Calcium hydroxide would serve both purposes of providing the catalyst and hydroxyl ions to provide the required alkalinity.

In accordance with this invention the source of the catalytic calcium ions in the aqueous reaction mixture is provided by adding calcium salts of maleic and tartaric acids wherein the calcium is obtained from filter cakes formed from previous reaction mixtures. It has been found that the small amounts of by-products and residual HOPTC and DOOHC in the filter cakes do not upset the desired balance of the desired compounds in the final reaction product. Further, minor amounts of by-product malate, maleate fumarate and D,L-tartrate likewise are not deleterious to the use of recycled calcium salt forming cation. Fresh maleic and D,L-tartaric acids are added for makeup as needed to form a suitable reaction mixture.

HOPTC/DOOHC FORMATION

The first step is the synthesis of HOPTC/DOOHC mixtures by the reaction in aqueous medium of maleate and D,L-tartrate reactants comprising both monovalent cation and calcium salts of maleic acid and D,L-tartaric acid. As noted above, the total amount of maleate plus D,L-tartrate reactants in the aqueous reaction mixture will generally range from about 20% to about 70% by weight of the mixture, more preferably from about 50% to about 65% by weight. In accordance with this invention, calcium maleate is provided by first reacting maleic acid with calcium carbonate provided by earlier reactions as will be more fully described below. The D,L-tartrate is provided by hydroxylation of maleic anhydride in the presence of a catalyst and hydrogen peroxide by known means. One portion of the D,L-tartaric acid employed in the synthesis reaction is taken from the neutralized hydroxylation reaction product and another portion is provided by recycled calcium D,L-tartrate.

The molar ratio of maleic acid to D,L-tartaric acid in the reaction mixture will generally range from about 0.5:1 to 8:1, more preferably from about 0.8:1 to about 1.2:1. The ratio of reactants will control the ratio of HOPTC/DOOHC in the final product.

As noted above the synthesis reaction takes place in the presence of a catalyst comprising calcium cations. In the process of this invention calcium maleate formed by maleic acid and recycled calcium carbonate is the major source of the catalyst. In addition to the recycled calcium cations, "makeup" calcium cations can be added as calcium hydroxide in the form of an aqueous slurry so as to provide a total molar ratio of calcium cation to maleate of 1:1. However, the amount of calcium cation can vary greatly and may be such that the ratio of moles of calcium cations to total moles of maleic and D,L-tartaric acids in solution is less than 1. Any compound which yields calcium cations in solution can be employed as the "makeup" calcium cation source. Such compounds include calcium hydroxide and water soluble calcium salts. Calcium hydroxide is highly preferred since it acts as both a calcium cation source and an alkaline material as a source of hydroxide ion.

The hydroxide of a monovalent cation is also essentially added to the reaction mixture as a neutralizing agent. This neutralizing agent is usually added in an amount such that the ratio of moles of monovalent cations to total moles of D,L-tartaric acid plus the moles of maleic acid minus the moles of calcium cations ranges from about 2.1:1 to about 3.8:1. More preferably this ratio ranges from about 2.2:1 to about 3.3:1. The monovalent cation-containing neutralizing agent can be any hydroxide which upon addition to water yields monovalent neutralizing cations in solution. Such neutralizing agents include, for example, alkali metal, ammonium or substituted ammonium hydroxide. Sodium hydroxide is highly preferred.

Sufficient neutralizing agent which, in combination with "makeup" calcium hydroxide, is added to the synthesis reaction mixture to insure that the reaction mixture is over-neutralized. Thus, the reaction mixture in the process of this invention will generally have a pH within the range of from about 8.5 to 13, more preferably from about 10.5 to about 12.5. The aqueous reaction mixture, after the appropriate amounts of reactants, catalysts and neutralizing agent are combined is maintained at a temperature of from about 20° C. to about 120° C., preferably from about 70° C. to about 90° C. for a period of time sufficient to form a reaction product mixture containing the desired amounts of HOPTC and DOOHC. Reaction times of from about 0.5 to 24 hours, more preferably from about 1 to 4 hours, would generally be suitable for realizing acceptable yields of the 2 components of the desired mixture.

At completion of the reaction the mixture is quenched with water to cool it to a temperature in the range of 80° C. Addition of water also improves the handling of the viscous reaction mass.

CALCIUM CARBONATE PRECIPITATION

The reaction product from the above-described reaction is pH adjusted to bring the pH of the solution to a range of from about 10 to about 12, preferably about 10 to 10.5. The pH adjustment may be performed either in the precipitator or in a separate vessel if desired. Alternatively, calcium carbonate is removed by increasing the mole ratio of carbonate ion to calcium ion without change in pH.

The pH adjusted material is added to the precipitator and is maintained in the range of from about 85° C. to about 115° C., preferably from about 90° C. to about 105° C. Concurrently a solution of carbonate, preferably sodium carbonate, at a preferred concentration of about 25%, is added to the precipitator to provide an overall mole ratio of carbonate to calcium of 1.3:1.0.

A slurry forms and is subjected to separation procedures to provide a solution containing the desired mixture of HOPTC and DOOHC. Any suitable means may be provided to attain the separation of the precipitated calcium carbonate from the solution of HOPTC and DOOHC. Most conveniently it has been found to be easily separated by filtration either batchwise or continuously. Typical filter equipment such as belt or drum filter or a centrifuge is satisfactory to provide a filter cake in a reasonable amount of time for filtration.

Although this invention is described with respect to carbonate precipitation using the preferred sodium cation, it is to be understood that other suitable cations may also be employed. Other cations useful in the process of this invention include potassium, ammonium or substituted ammonium.

Other salts may be employed to obtain the calcium carbonate precipitate and include sodium bicarbonate and other alkali metal and ammonium carbonates and bicarbonates. During the precipitation it is preferable to remove water from the slurry to maintain the concentration of the organic salts in the range of about 30% to 50% by weight.

The wet cake from the separation is mechanically reslurried with water to form an approximately 50% calcium carbonate slurry for recycle and conversion to calcium maleate as described below.

CALCIUM MALEATE FORMATION

Before introduction into the synthesis reaction, the calcium carbonate precipitate obtained from the product as described above is preferably converted to calcium maleate by reaction with maleic acid. Alternatively the calcium carbonate can be converted to calcium maleate in the synthesis reactor prior to reuse of the calcium to make further mixtures of DOPTC and DOOHC.

Preferably, the maleic acid is prepared in situ prior to the addition of the carbonate. An aqueous medium is preheated to a temperature in the range of from about 60° C. to about 70° C., preferably about 65° C. and molten maleic anhydride (MAN in the attached drawing) is charged to the heated water while allowing the temperature to increase to about 75° C. To assure complete hydrolysis of the maleic anhydride, the solution is held for about 15 minutes after which recycled calcium carbonate slurry at about 50% solids is added at a rate slow enough to avoid uncontrolled foaming due to the evolution of carbon dioxide. During the addition of calcium carbonate the reaction mass is heated to a temperature in the range of from about 90° C. to about 100° C. and preferably about 95° C. The calcium maleate reaction is held at boiling for about 15 minutes to convert all of the calcium carbonate to calcium maleate. The mixture is then charged to the synthesis reactor as an aqueous slurry for the preparation of additional HOPTC and DOOHC. During transfer to the synthesis reactor water may be evaporated to reduce volume.

It is obvious that other schemes than that described above may also be followed. For example, hold tanks, mixing tanks and transfer tanks may be employed which are not described above. Other variations will occur to those knowledgeable in the art.

PURIFICATION

The filtrate obtained from the procedure to remove calcium carbonate by the addition of sodium carbonate is purified by extraction with methanol and water. Such purification is shown in U.S. Pat. No. 4,633,071 referred to above.

According to such patent the solution obtained after removal of calcium carbonate is thoroughly mixed with methanol. After settling, two layers form because the desired solution of HOPTC and DOOHC is less soluble in methanol than the impurities to be removed. The undesired solution is decanted and stripped of residual methanol. The residue is dissolved in water and extracted again with methanol.

After purification the product is concentrated so as to provide the desirable concentration of HOPTC and DOOHC solution for use as detergent builder or sequestrant. The concentrated material may also be dried by any typical means such as by spray drying, etc. to provide granular or particulate material which is the form traditionally employed.

To further illustrate the process of the present invention there is described below non-limiting preferred embodiments.

EXAMPLE 1

Preparation of calcium maleate by reaction of pure maleic anhydride, water and pure calcium carbonate.

a. Preparation of Maleic Acid

Into a 4-necked flask equipped with stirrer (120 rpm), addition funnel, reflux condenser and thermometer were mixed 39.2 g (0.4 mole) of maleic anhydride and 60 g of water. The mixture was heated to 90° C. to ensure complete conversion of the maleic anhydride to maleic acid.

b. Preparation of Calcium Maleate

Calcium carbonate, 24 g (0.24 mole) was added to the above solution at 90° C. over 15 minutes with carbon dioxide evolution being observed. At the end of the addition, the solution was cloudy with suspended solids. The solution was held at 90° C. and sampled for analysis at 10, 30, 60 and 120 minutes after completion of addition. Analytical results are shown below in Table I.

TABLE I

| Sample (Min) | Carbonate Analysis (by Chittick Method) | pH observed |
|---|---|---|
| 10 | 0.00% | 3.70 |
| 30 | 0.00% | 3.70 |
| 60 | 0.00% | 3.47 |
| 120 | 0.00% | 3.47 |

This example shows that in the presence of excess maleic acid, calcium carbonate may be smoothly and completely converted to calcium acid maleate and carbon dioxide by reaction with maleic acid.

EXAMPLE 2

The procedure of Example 1 was repeated except for using 39.2 g (0.4 mole) of maleic anhydride, 70 g of water and 32 g (0.32 mole) of calcium carbonate. Calcium carbonate was again added over 15 minutes and sampled for analysis as shown below in Table II.

TABLE II

| Sample (Min) | Carbonate Analysis (by Chittick Method) | pH observed |
|---|---|---|
| 10 | 0.043% | 3.31 |
| 30 | 0.027% | 3.37 |
| 67 | 0.017% | 3.27 |
| 92 | 0.000% | 3.28 |

This example shows that even at higher levels of calcium carbonate, carbonate removal as carbon dioxide is complete. No fumarate was observed (by NMR) in the product thereby indicating that the maleic acid was not isomerized under the conditions of this reaction.

EXAMPLE 3

Use of calcium carbonate filter cake in the preparation of calcium maleate and the synthesis of HOPTC/DOOHC mixtures.

Calcium carbonate recycle filter cake (38.2 g) obtained in accordance with the above-described process and having the analysis shown in Table III below was slurried with 40 g of water.

TABLE III

| COMPONENT | WEIGHT |
|---|---|
| Calcium carbonate | 24.80 g |
| Disodium D,L-tartrate | 0.31 g |
| Disodium fumarate | 0.38 g |
| Disodium maleate | 0.30 g |
| Disodium malate | 0.08 g |
| HOPTC | 4.81 g |
| DOOHC | 0.23 g |
| Water | 7.29 g |

Over a 40 min. period, this slurry was added to a mixture of maleic anhydride (39.2 g, 0.4 mole) and water (80 g) that had been heated to 60° C. to convert all the anhydride to maleic acid. While the mixture was held at 65° C. all the carbon dioxide was removed and calcium maleate was formed. An additional 0.5 g (0.005 mole) of calcium carbonate was added to make up the total amount of calcium needed in the synthesis reaction.

Calcium hydroxide (1.11 g, 0.015 mole), D,L-tartaric acid (45.4 g, 0.303 mole), 50% sodium hydroxide (92.48 g, 1.156 mole NaOH) and water (50 g) were placed in a 500 ml 4-neck flask equipped with a stirrer (120 rpm), thermometer, condenser and addition funnel. From previous synthesis of a HOPTC/DOOHC mixture as described above with respect to the attached drawing, a calcium D,L-tartrate wet cake (65.15 g) of the following analysis was then added:

TABLE IV

| COMPONENT | WEIGHT |
|---|---|
| Calcium D,L-tartrate | 25.67 g |
| Disodium malate | 0.26 g |
| Disodium fumarate | 1.17 g |
| Disodium maleate | 1.63 g |
| HOPTC | 18.18 g |
| DOOHC | 3.52 g |
| Water | 14.72 g |

The calcium maleate slurry prepared above was then added and the reaction mixture heated to 78° C. Within one hour the mixture turned to a clear solution. The reaction was stirred for 3½ hours at 78° C. 250 g water was added and the mixture cooled to 27° C. Acetic acid (12.9 g) was added to reduce the pH from 12.24 to 8.74.

The resulting mass was filtered giving a calcium D,L-tartrate filter cake (for recycle) and a clear filtrate. This filtrate was added to a solution of sodium bicarbonate (2.1 g), sodium carbonate (25.97 g) and water (90 g) at 55° C. The mixture was heated to 75° C. for one hour and then at 85° C. for an additional hour to precipitate calcium carbonate. The mixture was filtered hot giving a calcium carbonate wet cake and a filtrate. The filtrate contained the desired HOPTC and DOOHC products and had the following analysis:

TABLE V

| COMPONENT | WEIGHT |
|---|---|
| HOPTC | 22.09 |
| DOOHC | 5.38 |
| Disodium D,L-tartrate | 0.99 |
| Disodium maleate | 1.71 |
| Disodium fumarate | 1.70 |
| Disodium malate | 0.20 |

The reaction described above was repeated four more times, each time using the two filter cakes (the "D,L-tartrate cake" and the "carbonate cake") obtained from the previous reaction and recycled to the next synthesis reaction. In each case similar results were obtained. In all cases the synthesis reactions were run for three hours. The first hour of the reaction the temperature was about 80° C. and then during the last two hours it was held at 90° C. The desired product from each synthesis reaction after calcium D,L-tartrate removal was analyzed to determine its HOPTC and DOOHC content. The conversion efficiency of maleate was also calculated. The results of these analysis are presented in Table VI below.

TABLE VI

|  | First Reaction | First Recycle | Second Recycle | Third Recycle | Fourth Recycle |
|---|---|---|---|---|---|
| Initial Solids % in reaction | 34.0 | 28.0 | 28.0 | 43.0 | 45.0 |
| Final Solids % in reaction | 72.0 | 71.0 | 67.0 | 67.0 | 68.0 |
| Total HOPTC + DOOHC % | 72.5 | 71.6 | 68.0 | 67.0 | 69.8 |
| Ratio of HOPTC/DOOHC | 4.1 | 4.7 | 5.4 | 4.5 | 5.6 |
| Maleate Conv. % | 78.0 | 75.0 | 73.0 | 74.0 | 76.0 |

This example demonstrates that calcium carbonate wet cake prepared under synthesis conditions can be recycled into the synthesis reaction via calcium maleate formation without loss of conversion efficiency.

The foregoing description is given for clarity of understanding only and no unnecessary limitations should be understood therefrom, as modifications will be obvious to those skilled in the art.

I claim:

1. A process for preparing a mixture of the alkali metal salts of 1-hydroxy-3-oxa-1,2,4,5-pentane tetracarboxylic acid and 3,6-dioxa-1,2,4,5,7,8-octane hexacarboxylic acid by means of a calcium ion catalyzed reaction which comprises:
   a. reacting the salts of maleic and D,L-tartaric acids in alkaline medium;
   b. reducing the calcium content of said reaction product mixture to the extent that the molar ratio of calcium to the D,L-tartrate succinate reaction products is less than about 1:10 by precipitation of calcium carbonate;
   c. recovering the calcium carbonate removed in step (b) and recycling it to step (a) to prepare additional amounts of reaction product, and
   d. recovering and purifying the remainder of the reaction product from step (b).

2. A process of claim 1 wherein the calcium is removed from the reaction product in step b at a temperature of from about 85° C. to about 105° C.

3. A process of claim 1 wherein the calcium carbonate is formed in the reaction mixture by reaction with an alkali metal carbonate.

4. A process of claim 2 wherein the calcium carbonate is formed by reaction with an alkali metal bicarbonate.

5. A process of claim 3 wherein the alkali metal is sodium.

6. A process of claim 4 wherein the alkali metal is sodium.

7. A process of claim 1 further including the step of reacting the calcium carbonate recovered in step (c) with maleic acid to form a salt before recycle to step (a).

8. A process of claim 7 wherein the calcium maleate is added to the reaction mixtures of step (a) in the form of an aqueous slurry.

9. A process of claim 7 wherein the calcium carbonate is formed by reaction of calcium ions with carbon dioxide.

10. A process of claim 1 wherein the reaction medium of step (b) is maintained at a pH in the range of from about 10 to about 12.

11. A process of claim 1 wherein the mole ratio of carbonate to calcium in step (b) is 1.3:1.

12. A process of claim 1 wherein the solids content of the reaction mixture of step (a) is in the range of from 55% to about 60% by weight.

13. A process for preparing a mixture of the alkali metal of 1-hydroxy-3-oxa-1,2,4,5-pentane tetracarboxylic acid and 3,6-dioxa-1,2,4,5,7,8-octane hexacarboxylic acid which comprises the steps of:
   a. forming an aqueous reaction mixture comprising from about 20% to 60% by weight of both calcium and monovalent cation salts of maleic acid and D,L-tartaric acid, said mixture corresponding to the over-neutralized mixture which is formed by combining:
      (i) maleic and D,L-tartaric acids in a maleic to D,L-tartaric molar ratio of from about 0.5:1 to about 8:1;
      (ii) a source of calcium cations in an amount such that the molar ratio of calcium to D,L-tartaric acid ranges from about 0.1:1 to 2.0:1 with the ratio of moles of calcium to total moles of maleic and D,L-tartaric acid being less than 1; and (III) a neutralizing agent comprising an hydroxide of a monovalent cation in an amount such that the ratio of moles of monovalent cation to moles of maleic acid plus moles of D,L-tartaric acid minus moles of calcium ranges from about 2.1:1 to 3.8:1;

(b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts;

(c) treating the filtrate from step (b) with a carbonate whereby calcium carbonate precipitates;

(d) removing the calcium carbonate from the filtrate and recycling it to step (a) to prepare additional amounts of reaction product and (e) recovering and purifying the filtrate from step (d).

14. A process of claim 13 further including the step of reacting the calcium carbonate recovered in step (d) with maleic acid prior to recycle to step (a) to form calcium maleate.

15. A process of claim 13 wherein the carbonate is sodium bicarbonate.

16. A process of claim 14 wherein the mole ratio of carbonate to calcium in step (c) is 1.3:1.

17. A process of claim 13 wherein the neutralizing agent is sodium hydroxide.

* * * * *